(12) United States Patent
Silver

(10) Patent No.: US 7,477,377 B2
(45) Date of Patent: Jan. 13, 2009

(54) DENSE PATTERN OPTICAL MULTIPASS CELL

(75) Inventor: Joel A. Silver, Santa Fe, NM (US)

(73) Assignee: Southwest Sciences Incorporated, Santa Fe, NM (US)

(*) Notice: Subject to any disclaimer, the term of this patent is extended or adjusted under 35 U.S.C. 154(b) by 178 days.

(21) Appl. No.: 10/896,608

(22) Filed: Jul. 21, 2004

(65) Prior Publication Data
US 2006/0232772 A1 Oct. 19, 2006

(51) Int. Cl.
G01N 1/10 (2006.01)
(52) U.S. Cl. .................. 356/246; 356/440
(58) Field of Classification Search ............... 356/244, 356/246, 432–440, 301; 250/343, 576
See application file for complete search history.

(56) References Cited

U.S. PATENT DOCUMENTS

| | | | |
|---|---|---|---|
| 3,253,226 A * | 5/1966 | Herriott et al. ............. 359/346 |
| 4,017,185 A | 4/1977 | Chupp |
| 4,127,329 A * | 11/1978 | Chang et al. ............... 356/301 |
| 4,676,639 A | 6/1987 | Van Wagenen |
| 4,783,789 A * | 11/1988 | Higgins ..................... 372/97 |
| 4,934,816 A * | 6/1990 | Silver et al. ................. 356/409 |
| 5,291,265 A | 3/1994 | Kebabian |
| 5,550,375 A | 8/1996 | Peters et al. |
| 5,726,752 A * | 3/1998 | Uno et al. .................. 356/246 |
| 5,734,165 A * | 3/1998 | Unal et al. ............... 250/338.1 |
| 6,087,181 A * | 7/2000 | Cong ......................... 436/37 |
| 6,654,163 B1 * | 11/2003 | Du et al. .................... 359/347 |
| 6,940,600 B1 * | 9/2005 | Smith ........................ 356/437 |
| 7,012,696 B2 * | 3/2006 | Orr et al. .................... 356/454 |
| 2002/0185603 A1 | 12/2002 | Daly et al. |
| 2004/0169863 A1 * | 9/2004 | Kawate ..................... 356/432 |

FOREIGN PATENT DOCUMENTS

| | | |
|---|---|---|
| DE | 29 06 536 | 9/1980 |
| DE | 102 16 047 A1 | 10/2003 |
| FR | 2 767 195 | 2/1999 |

OTHER PUBLICATIONS

Abdullin, R. M., et al., "Use of an Integrating Sphere as a Multipass Optical Cell", *Sov. J. Opt. Technol.*, vol. 55, No. 3, (Mar. 1988), 139-141.
Altmann, J., et al., "Two-Mirror Multipass Absorption Cell", *Appl. Opt.*, vol. 20, No. 6, (Mar. 15, 1981),995-999.

(Continued)

*Primary Examiner*—Hoa Q Pham
(74) *Attorney, Agent, or Firm*—Jeffrey D. Myers; Samantha A. Updegraff; Peacock Myers, P.C.

(57) ABSTRACT

A multiple pass optical cell and method comprising providing a pair of opposed cylindrical mirrors having curved axes with substantially equal focal lengths, positioning an entrance hole for introducing light into the cell and an exit hole for extracting light from the cell, wherein the entrance hole and exit hole are coextensive or non-coextensive, introducing light into the cell through the entrance hole, and extracting light from the cell through the exit hole.

18 Claims, 10 Drawing Sheets

OTHER PUBLICATIONS

Chernin, S. M., et al., "Optical Multipass Matrix Systems", *Appl. Opt.*, vol. 30, No. 1, (Jan. 1991),51-58.

Hao, Lu-Uyan, et al., "Cylindrical Mirror Multipass Lissajous System for Laser Photoacoustic Spectroscopy", *Rev. Sci. Instrum.*, Vol. 73, No. 5, (May 2002),2079-2085.

Herriott, Donald R., et al., "Folded Optical Delay Lines", *Appl. Opt.*, vol. 4, No. 8, (Aug. 1965),883-889.

Herriott, Donald R., et al., "Off-Axis Paths in Spherical Mirror Interferometers", *Appl. Opt.*, vol. 3, No. 4, (Apr. 1964),523-526.

McManus, J. B., et al., "Astigmatic Mirror Multipass Absorption Cells for Long-Path-Length Spectroscopy", *Appl. Opt.*, vol. 34, No. 18, (Jun. 20, 1995),3336-3348.

McManus, J. B., et al., "Narrow Optical Interference Fringes for Certain Setup Conditions in Multipass Absorption Cells of the Herriott Type", *Appl. Opt.*, vol. 29, No. 7, (Mar. 1, 1990),898-900.

Salour, Michael M., "Multipass Optical Cavities for Laser Spectroscopy", *Laser Focus*, (Oct. 1977),50-55.

Sigrist, M. W., et al., "Laser Spectroscopic Sensing of Air Pollutants", *Proc. SPIE*, vol. 4063,(2000),17-25.

Trutna, W. R., et al., "Multiple-Pass Raman Gain Cell", *Appl. Opt.*, vol. 19, No. 2, (Jan. 15, 1980),301-312.

White, John U., "Long Optical Paths of Large Aperture", *J. Opt. Soc. Am.*, vol. 21, (May 1942),285-288.

Yariv, Amnon, "The Propogation of Rays and Spherical Waves", *Introduction to Optical Electronics*, Holt, Reinhart, and Winston, Inc., New York, Chap. 2, (1971),18-29.

Mittenzwey, K-H, et al., "A Portable Absorption-Fluorometer for Detection of Organic Substances in Fluids", *Fresenius J. Anal. Chem.*, vol. 355, (1996),742-744.

Yao, Lu-Yuan, et al., "Cylindrical Mirror Multipass Lissajous System for Laser Photoacoustic Spectroscopy", *Rev. of Scientific Instruments*, vol. 73, No. 5, (May 2002),2079-2085.

* cited by examiner

DENSE PATTERN OPTICAL MULTIPASS CELL

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of Small Business Research (SBIR) Contracts No. DE-FG02-03ER83779 and NNA04CB22C, awarded by the U.S. Department of Energy and NASA, respectively.

CROSS-REFERENCE TO RELATED APPLICATIONS

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to creation and use of long folded optical paths in a compact structure for use with lasers in making optical measurements or systems.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Multiple pass optical cells with dense spot patterns are very useful for many applications, especially when the cell volume must be minimized relative to the optical path length. Present methods to achieve these dense patterns require very expensive, highly precise astigmatic mirrors and complex alignment procedures to achieve the desired pattern. This invention describes a new, much simpler and less demanding mirror system comprising inexpensive cylindrical mirrors which can meet all of the requirements and be aligned much more readily.

Multiple pass optical cells are used to achieve very long optical path lengths in a compact footprint and have been extensively used for absorption spectroscopy, (White, J. U., "Long Optical Paths of Large Aperture," *J. Opt. Soc. Am.*, vol. 32, pp 285-288 (May 1942); Altmann, J. R. et al., "Two-mirror multipass absorption cell," *Appl. Opt.*, vol. 20, No. 6, pp 995-999 (15 Mar. 1981)), laser delay lines (Herriott, D. R., et al., "Folded Optical Delay Lines," *Appl. Opt.*, vol. 4, No. 8, pp 883-889 (August 1965)), Raman gain cells (Trutna, W. R., et al., "Multiple-pass Raman gain cell," *Appl. Opt.*, vol. 19, No. 2, pp 301-312 (15 Jan. 1980)), interferometers (Herriott, D. H., et al., "Off-Axis Paths in Spherical Mirror Interferometers," *Appl. Opt.*, vol. 3, No. 4, pp 523-526 (April 1964)), photoacoustic spectroscopy (Sigrist M. W., et al., "Laser spectroscopic sensing of air pollutants," *Proc. SPIE*, vol. 4063, pp. 17 (2000)) and other resonators (Yariv, A., "The Propagation of Rays and Spherical Waves," from *Introduction to Optical Electronics*, Holt, Reinhart, and Winston, Inc., New York (1971), Chap. 2, pp 18-29; Salour, M. M., "Multi-pass optical cavities for laser spectroscopy," *Laser Focus*, 50-55 (October 1977)).

These cells have taken the form of White cells (White, J. U., "Long Optical Paths of Large Aperture," *J. Opt Soc. Am.*, vol. 32, pp 285-288 (May 1942)), integrating spheres (Abdullin, R. M. et al., "Use of an integrating sphere as a multiple pass optical cell," Sov. *J. Opt. Technol.*, vol. 55, No. 3, pp 139-141 (March 1988)), and stable resonator cavities (Yariv, A., "The Propagation of Rays and Spherical Waves," from *Introduction to Optical Electronics*, Holt, Reinhart, and Winston, Inc., New York (1971)).

The stable resonator is typified by the design of Herriott (Herriott, D. H., et al., "Off-Axis Paths in Spherical Mirror Interferometers," *Appl. Opt.*, vol. 3, No. 4, pp 523-526 (April 1964)). The simplest such Herriott cell consists of two spherical mirrors of equal focal lengths separated by a distance d less than or equal to four times the focal lengths f of the mirrors. This corresponds to stable resonator conditions. A collimated or focused laser beam is injected through the center of a hole in one of the mirrors, typically an off-axis location near the mirror edge. The beam is periodically reflected and refocused between these mirrors and then exits through the center of the input hole (defining the re-entrant condition) after a designated number of passes N, in a direction (slope) that is different from the entry slope. As a result, the total optical path traversed in the cell is approximately N×d. The pattern of reflected spots observed on the mirrors in these cells forms an ellipse. Re-entrant conditions for spherical mirror Herriott cells are restricted by certain predetermined ratios of the mirror separation d to the focal length f and the location and slope of the input beam. For any re-entrant number of passes N, all allowed solutions are characterized by a single integer M. Excellent descriptions for the design, setup and use of these cells are given by Altmann (Altmann, J. R., et al., "Two-mirror multipass absorption cell," *Appl. Opt.*, vol. 20, No. 6, pp 995-999 (15 Mar. 1981)) and McManus (McManus, J. B., et al., "Narrow optical interference fringes for certain setup conditions in multipass absorption cells of the Herriott type," *Appl. Opt.*, vol. 29, No. 7, pp 898-900 (1 Mar. 1990)).

When the cell volume must be minimized relative to the optical path length or where a very long optical path (>50 m) is desired, it is useful to increase the density of passes per unit volume of cell. The conventional spherical mirror Herriott cell is limited by the number of spots one can fit along the path of the ellipse without the spot adjacent to the output hole being clipped by or exiting that hole at a pass number less than N. This approximately restricts the total number of passes to the circumference of the ellipse divided by the hole diameter, which in turn is limited by the laser beam diameter. For a 25-mm radius mirror with a relatively small 2-mm diameter input hole located 20 mm from the center of the mirror, a maximum of about $(\pi \times 2 \times 20)/2 \approx 60$ spots, or 120 passes is possible at best. Generally the hole is made larger to prevent any clipping of the laser input beam that might lead to undesirable interference fringes, and typical spherical Herriott cells employ less than 60 passes.

Herriott (Herriott, D. R. and Schulte, H. J., "Folded Optical Delay Lines," *Appl. Opt.*, vol. 4, No. 8, pp 883-889 (August 1965)) demonstrated that the use of astigmatic mirrors could greatly increase the spot density, and hence optical path length, in the cell. Each mirror has different finite focal lengths ($f_x$ and $f_y$) along orthogonal x and y axes, and the mirrors are aligned with the same focal lengths parallel to one another. The resulting spots of each reflection on the mirrors create precessions of ellipses to form Lissajous patterns. Since these patterns are distributed about the entire face of each mirror, many more spots can be accommodated as compared to a cell with spherical mirrors. Herriott defines the method of creating the astigmatic mirror is to distort a spherical mirror, either in manufacture or in use, by squeezing a spherical mirror in its mount. He states that the amount of astigmatism required is very small and amounts to only a few wavelengths. McManus (McManus, et al., "Astigmatic mirror multipass absorption cells for long-path-length spectroscopy," Appl. Opt., vol. 34, No. 18, pp 3336-3348 (20 Jun. 1995)) outlines the theory and behavior of this astigmatic Herriott cell and shows that the density of passes can be increased by factors of three or more over spherical mirror cells. For these astigmatic mirror cells, light is injected through a hole in the center of the input mirror. Allowed solutions for re-entrant configurations are characterized by a pair of integer indices $M_x$ and $M_y$, since there are now two focal lengths present along orthogonal axes.

The drawback of this design is that the constraints to achieve useful operation are very severe. First of all, both $M_x$ and $M_y$ must simultaneously be re-entrant, so that for a desired N and variable distance d, the focal lengths $f_x$ and $f_y$, must be specified to a tolerance of 1 part in $10^4$. Since mirrors can rarely be manufactured to such tolerances, this cell as originally proposed is impractical for routine use. However, Kebabian (U.S. Pat. No. 5,291,265 (1994)) devised a method to make the astigmatic cell usable. Starting with the astigmatic Herriott setup with the same mirror axes aligned, he then rotates one mirror around the z-axis (FIG. 2), thereby mixing the (previously independent) x and y components of the beam co-ordinates. A moderate rotation of ~5-20 degrees and a small compensating adjustment of the mirror separation distance can accommodate the imprecision in the manufacturing of the mirror focal lengths. However, this approach is still difficult to achieve in practice and requires complex calculations and skill to get to the desired pattern. Furthermore, the astigmatic mirrors must still be custom made and cost many thousands of dollars for a single pair.

Recently, Hao (Hao, L.-Y., et. al., "Cylindrical mirror multipass Lissajous system for laser photoacoustic spectroscopy," Rev. Sci. Instrum., vol. 73, No. 5, pp. 2079-2085 (May 2002)) described another way to generate dense Lissajous patterns using a pair of cylindrical mirrors, each having a different focal length, and where the principal axes of the mirrors are always orthogonal to one another. In essence, this creates a pair of mirrors whose x-axis comprises one curved surface (mirror A) of focal length $f_x$ and one flat mirror surface (mirror B), and in the y-axis comprises one flat mirror surface (on mirror A) and one curved surface of focal length $f_y$ (mirror B), where $f_x \neq f_y$. Formulas to predict the spot patterns on each mirror are provided. The advantage to this system is that the dense Lissajous patterns can be formed from a pair of inexpensive mirrors, in contrast to the requirement for custom astigmatic mirrors (we note that for a practical commercial multipass cell, one cannot rely on simply squeezing spherical mirrors to achieve a reliable long term, stable set of focal lengths. Thus diamond turned custom astigmatic mirrors must be made). The drawback of this mismatched focal length pair of cylindrical mirrors is that, similar to the astigmatic Herriott cell, for a given pair of focal lengths, there is only one allowed re-entrant solution value of N permitted. Of course, for photoacoustic measurements as intended by Hao, where any exiting light is not detected, the light does not necessarily have to be re-entrant and many values of mirror separation which are not re-entrant, but do generate many passes, are useful.

The present invention describes a simple, low cost and more easily aligned high density multipass optical cell, where many different paths can be achieved with the same set of mirrors. The key to this invention is the use of cylindrical mirrors with nominally equal focal lengths. When two cylindrical mirrors are aligned such that the curved axes are crossed at 90 degrees (orthogonal condition), they generate spot patterns similar to a spherical Herriott cell, except that the stable resonator conditions restrict the allowed separations to $0 < d \leq 2f$. If the entry point of the laser beam is off the central axis, elliptical spot patterns similar to a spherical cell are generated; if the beam enters through the center of one mirror, then lines instead of ellipses form and different re-entry restrictions apply.

The present invention has also determined that, by rotating the cylindrical mirrors to angles δ other than 90 degrees, the previously elliptical or linear spot patterns degenerate into dense Lissajous patterns of spots that generally fill a rectangularly-spaced region of each mirror. Without complex alignment procedures, and starting from a predetermined 90 degree crossed pattern, one can readily generate predicted dense patterns and much longer optical path lengths by twisting either mirror over the unrestricted range of rotation angle δ. This works for both off-axis and central axis input holes and almost any value of N can be achieved within the stability constraints for d and at almost any rotation. Unlike the astigmatic cell or mismatched cylindrical cell, achieving alignment of these spot patterns does not rely on the absolute manufactured focal lengths, but only on the easily adjusted ratio d/f and relative twist angle of the two cylindrical axis planes.

BRIEF SUMMARY OF THE INVENTION

The present invention is of a multiple pass optical cell and method comprising: providing a pair of opposed cylindrical mirrors having curved axes with substantially equal focal lengths; positioning an entrance hole for introducing light into the cell and an exit hole for extracting light from the cell, wherein the entrance hole and exit hole are coextensive or non-coextensive; introducing light into the cell through the entrance hole; and extracting light from the cell through the exit hole. In the preferred embodiment, the curved axes are crossed at angles other than approximately 0, 90, 180, and 270 degrees. A rotation mount is provided for one of the mirrors permitting rotation of the curved axes with respect to one another. A plurality of number of passes of light between the two mirrors exist for light entering the entrance hole and exiting the exit hole for any given combination of mirror separation distance and angle of crossing of the curved axes. Manufacturing tolerances as to the focal lengths are adjusted for by varying mirror separation distance.

The invention is also of a multiple pass optical cell and method comprising: providing a pair of opposed cylindrical mirrors having curved axes crossed at angles other than approximately 0, 90, 180, and 270 degrees; positioning an entrance hole for introducing light into the cell and an exit hole for extracting light from the cell, wherein the entrance hole and exit hole are coextensive or non-coextensive; introducing light into the cell through the entrance hole; and extracting light from the cell through the exit hole. In the preferred embodiment, the curved axes have substantially equal focal lengths. A rotation mount is provided for one of the mirrors permitting rotation of the curved axes with respect to one another. A plurality of number of passes of light between the two mirrors exist for light entering the entrance hole and exiting the exit hole for any given combination of mirror separation distance and angle of crossing of the curved axes. Manufacturing tolerances as to the focal lengths are adjusted for by varying mirror separation distance.

A primary object of the present invention is to generate a very long optical path in a compact cell.

Another object of the invention is to keep the cost of this cell low so as to permit widespread commercial availability and feasibility.

Another object of this invention is to make a dense multipass cell where one set of mirrors permits a wide range of configurations having many different numbers of allowed passes.

Another object of this invention is to make alignment of the desired number of optical passes easier, quicker and more reliable to accomplish.

Another objective is to permit a long optical path laser feedback configuration.

A primary advantage of the present invention is that it can be used in a wide variety of optical applications and can be constructed at significantly lower cost as compared with other dense pattern optical designs.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention describes a simple, low cost and more easily aligned high density multipass optical cell, where many different paths can be achieved with one set of mirrors. The key to this invention is the use of cylindrical mirrors with nominally equal focal lengths. When two cylindrical mirrors are aligned such that the curved axes are crossed at 90 degrees, they generate spot patterns similar to a spherical Herriott cell, except that the stable resonator conditions restrict the allowed separations to $0<d\leq 2f$. If the entry point of the laser beam is off the central axis, elliptical spot patterns similar to a spherical cell are generated; if the beam enters through the center of one mirror, then lines instead of ellipses form and different re-entry restrictions apply. This mirror is also useful where non re-entry, and long paths are required.

For purposes of the specification and claims, a "cylindrical mirror" is one for which one radius of $r_x$ and $r_y$ is substantially infinite, the non-infinite axis being known as the "curved axis". This is in contradistinction to a "flat mirror", for which both radii are substantially infinite, and a "spherical mirror" for which both radii are non-infinite and substantially equal. An "astigmatic mirror" is a mirror for which both radii are non-infinite but not equal, usually deviating slightly from one another by design.

The present invention includes rotating the cylindrical mirrors to angles other than 90 degrees, such that the previously elliptical or linear spot patterns degenerate into dense Lissajous patterns of spots that generally fill a rectangularly-spaced region of each mirror. Without complex alignment procedures, and starting from a 90 degrees crossed pattern, one can readily generate known dense patterns and much longer optical path lengths by twisting either mirror over the full range of rotation angles δ. This works for both off-axis and central axis input holes and almost any value of N can be achieved within the stability constraints for d and at almost any rotation. Specific re-entrant conditions have been identified and are easily set by various combinations of mirror separation and angle between the plane of the curved axis of each mirror.

Figure 1:
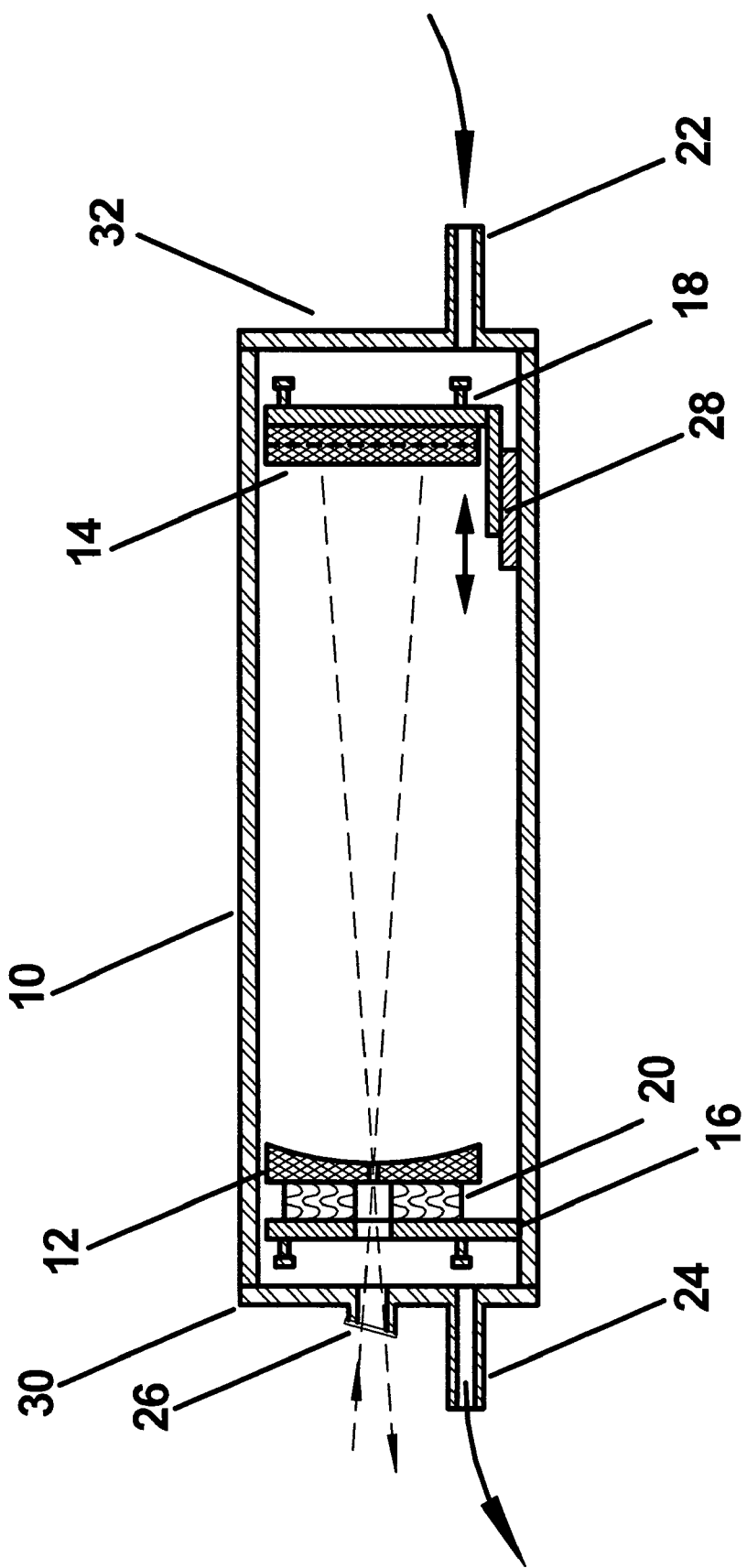
FIG. 1 is a drawing of the preferred embodiment of the present invention.

FIG. 1 is a drawing of the preferred embodiment for the present invention. The cylindrical mirrors 12 and 14 are attached to adjustable-tilt mirrors mounts 16 and 18, respectively, which are attached to an open frame or closed cell 10 separated by distance d. In this example, one of the mirror mounts is attached to a means 28 to permit variable adjustment of the mirror separation. Mirror 12 is first attached to a rotation mount 20 along the central axis of the cell so as to so as to be able to rotate this mirror over the full 2π angular range around the central axis relative to the other mirror 14. A light source or laser is pointed into the cell at the appropriate direction (slope) and a detector mounted outside the cell collects the light after transmission through the multiple pass optics. In the case of a closed cell, the gas is input at one end 22 and pumped out through a second port 24 at the other end. In this case sealed end flanges 32 and 30 are attached to the cell wall. A window 18 is used to permit the light to enter and exit the sealed cell so that no ambient gas can interfere with the gas sample inside the cell.

This description begins with a discussion of the prior art spherical Herriott cell theory and then briefly describes the prior art astigmatic cell design and restrictions to provide a basis for the new cylindrical cell invention.

Figure 2:
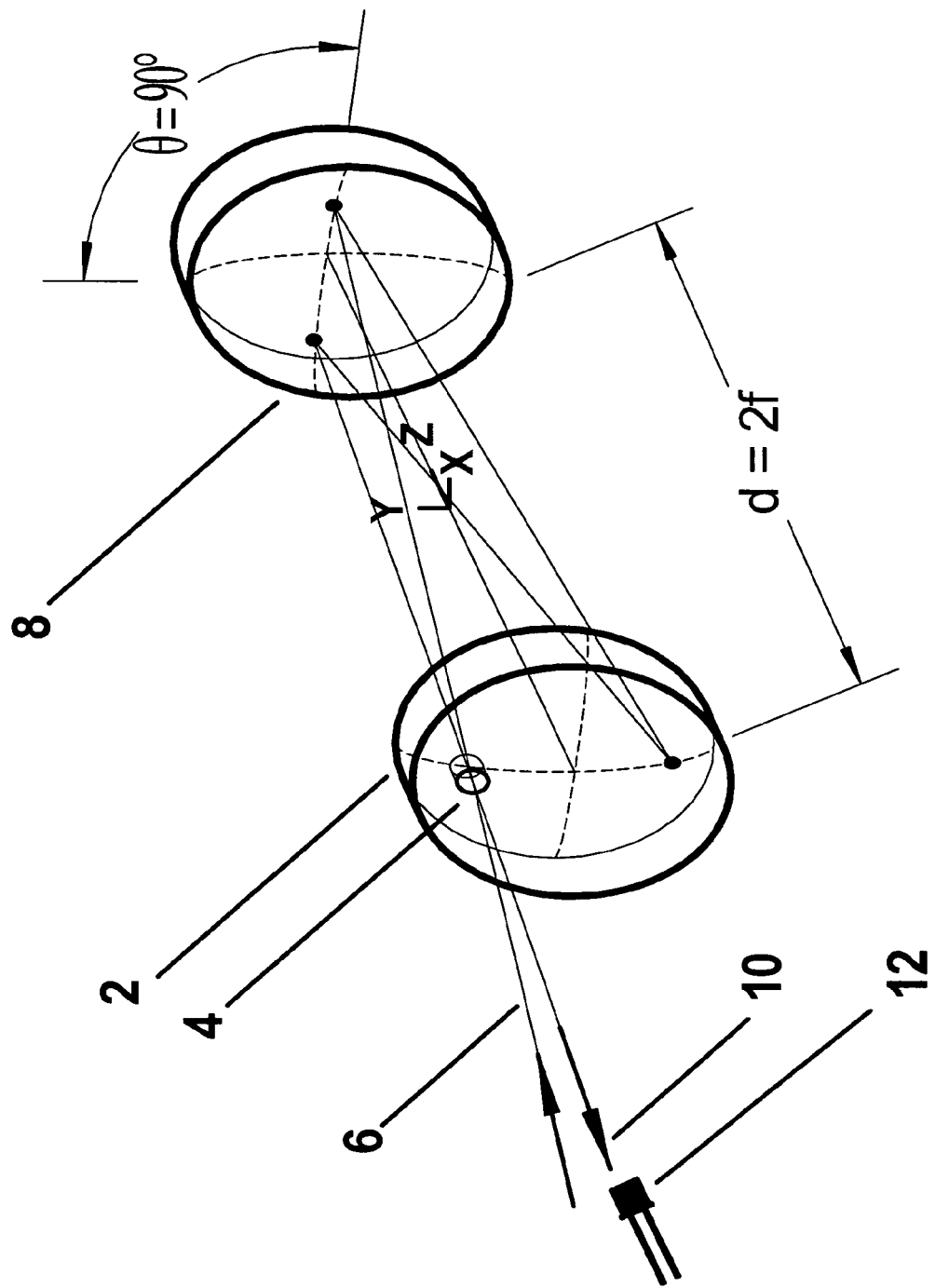
FIG. 2 is a drawing of a conventional spherical mirror Herriott cell.
Figure 3:
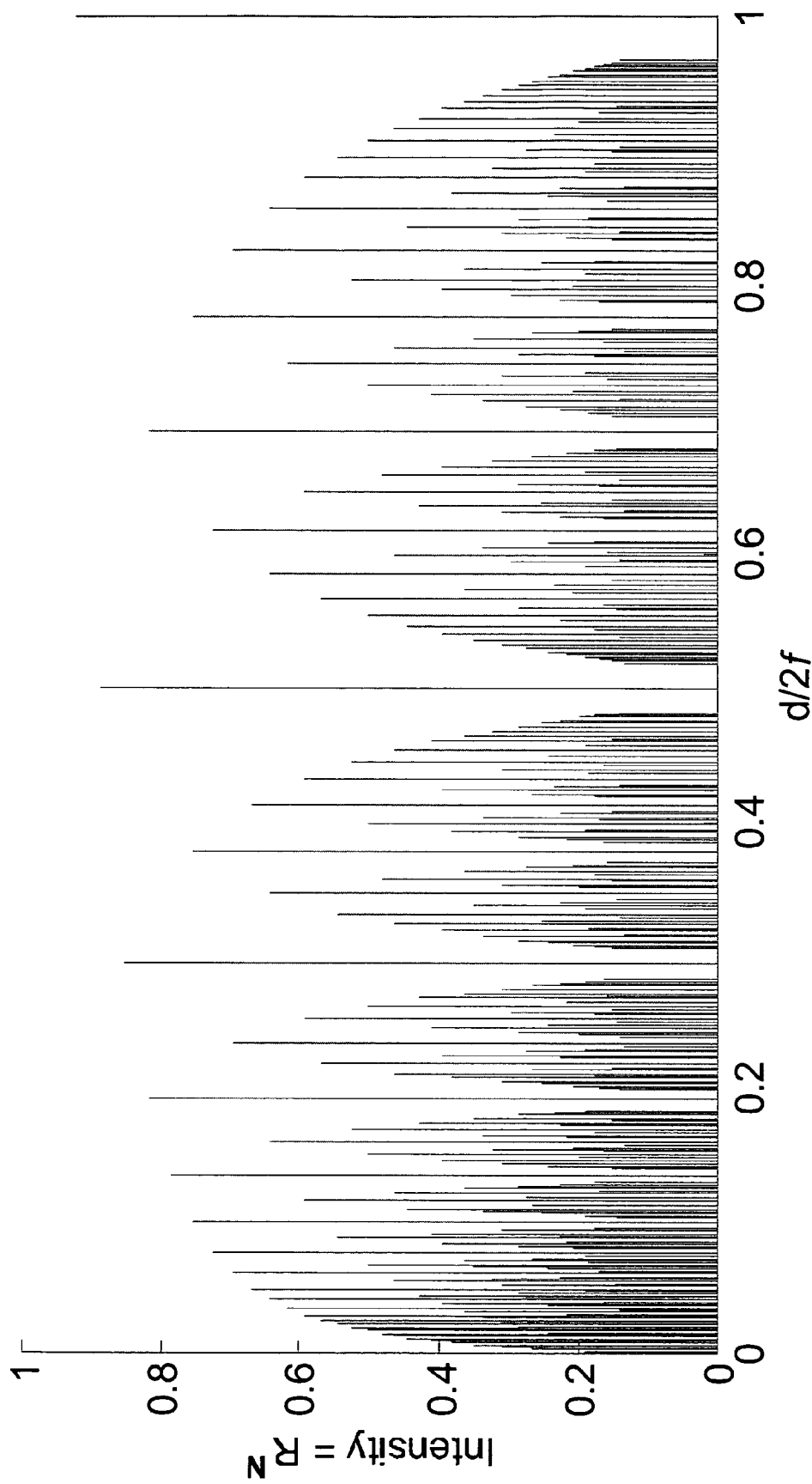
FIG. 3 is a plot of the patterns of allowed re-entrant passes for a spherical mirror Herriott cell as a function of dimensionless mirror separation d/2f. The transmitted intensity is equal to $R^N$, where R is the reflectivity of the mirrors (0.98 here) and N the total number of passes through the cell.

As generally set up (FIG. 2), the normal Herriott cell comprises one spherical mirror ("front") 2 of focal length f with an off-axis entrance hole 4 (at co-ordinates $x_0$ and $y_0$) through which the laser beam 6 is injected with slopes $x_o'$ and $y_o'$ and pointed at a second spherical mirror 8 ("rear"), also of focal length f. This beam is then periodically reflected and refocused such that the beam eventually exits 10 through the input hole 4 (re-entrant condition) but in the opposite direction (slope) of the input beam so as to make possible the placement of a Detector 12 without obstructing the input beam. The conditions for re-entry and the number of passes in the cell (even integer N) are governed by the focal lengths of the mirrors f, their separation d and the initial slopes of the input beam ($x_0'$ and $y_0'$) relative to the ratio of d/f. The total optical path within the cell is approximately d×N. The patterns of spots on the mirrors trace out an ellipse, where the co-ordinates of the spots of the $i^{th}$ pass are:

$$x_i = x_0 \cos(i\theta) + \sqrt{\frac{d}{4f-d}} (x_0 + 2fx_0')\sin(i\theta), \quad (1)$$

with a corresponding equation for y. Thus $x_i$ is the projection of the maximum excursion of the x co-ordinate of any spot (i.e., $x_{max}$) on either mirror. This position changes on each pass with an incremental increase i in the angle θ. For the off-axis injection of the laser beam as shown in FIG. 2, the light will exit the cell after an integral number of 2π multiples of θ, so that:

$\theta_R = 2\pi M/N$ and $d = 2f(1 - \cos \theta_R)$, (2)

where the number of complete orbits of spots before exiting is denoted by the integer index M; $\theta_R$ is the angular projection advance angle for each sequential pass. Thus after N passes, the spot pattern has rotated a multiple of 2π in both x and y co-ordinates and exits through the input hole. While many possible solutions for N and M exist for any given set of input conditions, the generally used initial conditions (with the off-axis input hole defined as $x_0=0$, $y_0=1$) is to align the first pass at $x_1=1$, $y_1=0$ (i.e., input slopes corresponding to $x_0'=1$, $y_0'=-1$ in reduced units of d/2f). This condition generates a circle with N=4 at d=2f. This is illustrated in FIG. 2. Under these conditions, all patterns can be characterized by:

$N = 4M \pm K$, (3)

where K is an even integer, and positive K correspond to solutions of d<2f and negative K to solutions for d>2f (up to a maximum allowed separation of 4f). In general, −K solutions are not as useful since the beam patterns trend toward being much larger in size than the input hole position as the mirror separation increases beyond 2f. While many different (M, N) pairs can generate the same fraction (angular advance θ) in Eqn. 2, only the set with the lowest N is allowed. All other sets cannot be achieved since the pattern will exit at a pass number less than N. For example, M=2, N=10 gives a fraction of ⅕ and θ=0.4π. Since M=4 and N=20 also gives a fraction of ⅕, this 20-pass configuration can't be achieved because the beam would exit after the tenth pass. As further elaborated by McManus, these rules can be formalized by computing modulo orders of the corresponding K values for any N (McManus, J. B. and Kebabian, P. L., "Narrow optical interference fringes for certain setup conditions in multipass absorption cells of the Herriott type," *Appl. Opt.*, vol. 29, No. 7, pp 898-900 (1 Mar. 1990). FIG. 3 illustrates the pattern of allowed solutions for the spherical Herriott cell as a function of the ratio d/2f. For d>2f, the pattern is just a mirror image reflected about d=2f. The relative intensity of the light exiting the cell is related to N by $R^N$, where R=0.98 is the mirror reflectivity in this calculation. The patterns of allowed passes correspond to various families of {N, M, K}.

The useful properties of the spherical Herriott cell are that virtually any desired optical path length and number of passes can be achieved by simply adjusting the mirror separation distance. The output spot position and slope are fixed regardless of the spot pattern or number of passes, and that this output is invariant to slight tilt or misalignment of the mirrors. Thus once the initial beam is aligned and the detector located, the number of passes and path length are readily adjusted by simply moving the position of the rear mirror along the axis.

High Density Cells

In order to achieve a higher density of spots, which leads to longer paths lengths for the same sized cell, Herriott developed a multipass optical cell using a pair of matched astigmatic mirrors (Herriott, D. R. and Schulte, H. J., "Folded Optical Delay Lines," *Appl. Opt.*, vol. 4, No. 8, pp 883-889 (August 1965)). Each mirror has a different finite focal length along its orthogonal x and y axes, $f_x$ and $f_y$. Thus unlike the spherical cell, the astigmatic cell x and y co-ordinates have separate, independent solutions. With the input hole now in the center of the mirror, the x and y co-ordinates for the $i^{th}$ spot are defined by:

$x_i = X_{max} \sin(i\theta_x)$, $y_i = Y_{max} \sin(i\theta_y)$, $\theta_x = \cos^{-1}(1 - d/2f_x)$, and $\theta_y = \cos^{-1}(1 - d/2f_y)$, (4)

where $X_{max}$ and $Y_{max}$ are the maximum positions of x and y in the spot pattern. The re-entrant solutions for $M_x$ and $M_y$ are slightly different than in Eqn. (2), $\theta_{xR} = \pi M_x/N$, and $\theta_{yR} = \pi M_y/N$, (5)

because the beam can exit after only π radians, rather than a full 2π when the input hole is at the edge of the pattern. M here can be viewed as the number of half-orbits of spots before each co-ordinate exits. As a result, the allowed indices are now defined here by:

$N = 2M_x + K_x = 2M_y + K_y$. (6)

Thus, to achieve re-entrant conditions, two simultaneous equations must be solved for a desired set of [N, $M_x$, $M_y$]. This results in specific design values for d, $f_x$ and $f_y$, making the system much less flexible for being able to select N given a particular set of mirrors. This is in contrast to the normal spherical Herriott cell where the ratio of d/f can be adjusted to give a range of thetas, and thus a series of many differing re-entrant spot patterns for a given mirror pair. Since both half and full orbits of the spot patterns can be re-entrant, the beam can exit into any quadrant of x-y space. Optimal solutions can be found where the beam exits in a plane opposite the input beam onto a unique, fixed position, where patterns minimize spots near the input hole and where common factors (lower order exits at passes <N) are avoided. These solutions have been determined to require that N/2 be an odd integer and $M_x$ and $M_y$ be even integers.

In order to achieve a re-entrant design, manufacturing criteria on the precision for d, $f_x$ and $f_y$ are so severe that a commercially produced cell is almost impossible to make reliably and repeatedly. The focal lengths must be precise to better than 1 part in $10^4$. Kebabian (U.S. Pat. No. 5,291,265 (1994)) devised a method to make the astigmatic cell usable by rotating the axis of one astigmatic mirror relative to the other and thereby mixing the (previously independent) x and y components of the beam co-ordinates. A moderate rotation of ~5-20 degrees and a small compensating adjustment of the mirror separation distance can accommodate the imprecision in the manufacturing of the mirror focal lengths. However, this approach is still difficult to achieve in practice and requires complex calculations and skill to get to the desired pattern. Furthermore, the astigmatic mirrors must be custom made and cost many thousands of dollars for a single pair.

Numerical Determination of Spot Patterns

In all of these Herriott-style systems, the precise patterns of spot locations can be computed either directly from matrix multiplication methods or from analytic solutions of the relevant ray tracing equations derived from these matrices.

Using ray matrix theory as outlined by Yariv (Yariv, A., "The Propagation of Rays and Spherical Waves," from Introduction to Optical Electronics, Holt, Reinhart, and Winston, Inc., New York (1971), Chap. 2, pp 18-29), the propagation of light rays through an optical system is readily understood. Given the $x_o$ and $y_o$ components and respective slopes $x_o'$ and $y_o'$ of the incident ray, the positions and slopes after each action (translation, reflection, etc.) are:

$$r_{i+1} = \begin{bmatrix} x_{i+1} \\ x'_{i+1} \\ y_{i+1} \\ y'_{i+1} \end{bmatrix} = M \cdot r_i = [4 \times 4] \begin{bmatrix} x_i \\ x'_i \\ y_i \\ y'_i \end{bmatrix}, \quad (7)$$

where the $(i+1)^{th}$ vector r is related to the previous pass i by a square matrix M that represents coefficients that perform the specified optical operation. For the specific case of two mirrors, we can find the position and slopes of the ray after one round-trip of the cell, denoted by index n, as the product of $R_1 \cdot D \cdot R_2 \cdot D \equiv C$, where R is a reflection matrix, D a translation matrix and the subscripts 1 and 2 correspond to each of the two mirrors. For n round trips, then we can express $r_n = C^n \cdot r_o$.

If the x and y components are uncoupled, then we can use separate 2×2 matrices for each x and y component. Thus the four elements of the solution C can be expressed as:

$$C = \begin{bmatrix} A & B \\ C & D \end{bmatrix}, \quad (8)$$

The relevant matrices for translation and reflection, where f is the focal length (radius of curvature/2) along the specified component axis and d the separation, are:

$$D = \begin{bmatrix} 1 & d \\ 0 & 1 \end{bmatrix} \quad (9)$$

and $$R = \begin{bmatrix} 1 & 0 \\ -1/f & 1 \end{bmatrix}.$$

From the equations above, C can be computed using matrix multiplication and the resulting elements of C used to derive a recursive solution for each 2×2 operation for x (or similarly y) as:

$$x_{n+2} - 2bx_{n+1} + \gamma x_n = 0,$$

where $b = \frac{1}{2}(A+D)$ and $\gamma = AD - BC = 1.$ (10)

It can also be shown that $b = \cos(2\theta)$, where $2\theta$ is twice the advance angle defined in Eqn. 1, since this formulation is describing a round-trip of two sequential passes. The stability criterion for $\theta$ to be real also creates the restriction $|b| \leq 1$. The angle theta is the centroid of revolution of the x or y component.

For the prior art astigmatic Herriott cell (without rotation of the mirrors), there are different solutions for $\theta_x$ and $\theta_y$, so that re-entrant solutions must satisfy two simultaneous equations.

If the principal axis of a non-spherical mirror is not aligned with x or y, but twisted by an angle δ, then a 4×4 matrix must be used to include cross-terms (coupling of x and y) and the rotation matrix for this situation is defined by $R' = T(-\delta) \cdot R \cdot T(\delta)$, $$T(\theta_{tw})(\delta) = \begin{bmatrix} \cos\delta & 0 & \sin\delta & 0 \\ 0 & \cos\delta & 0 & \sin\delta \\ -\sin\delta & 0 & \cos\delta & 0 \\ 0 & -\sin\delta & 0 & \cos\delta \end{bmatrix}. \quad (11)$$

This rotated reflection matrix and its corresponding 4×4 translation matrix must be used when either mirror is rotated away from an orthogonal axis. Note that this matrix approach is general in nature and can be used for any two-mirror system.

Analytic Formulation

From the formulations presented above, generalized analytic solutions similar to Eqn. 10 can be derived for rotated mirror systems, where the positions of each spot for the $n^{th}$ round-trip are given by a recursion formula. Unfortunately, these are very complicated algebraic expressions and the matrix formulation for these systems is preferred.

Detailed Solutions for a Cylindrical Mirror System

Turning now to the present invention, define a cylindrical mirror cell (FIG. 4) as having a pair of cylindrical mirrors 2 and 4, each of which has a single finite focal length f in the arbitrarily defined x-z plane and is flat in the y-z plane. Define the starting point for this system with the two mirrors twisted at a relative angle of 90 degrees, so that the front mirror has curvature along the y axis and the rear mirror is curved along the x axis. Obviously this system will also work if x and y were reversed.

Since the curvatures of the two mirrors are orthogonal, this 90 degree crossed cylindrical system can be represented by 2×2 matrices using Eqn. 9 where the x-coordinate $R_1$ uses 0 and $R_2$ uses $1/f$ for the inverse focal lengths, and for the y-coordinate $R_1$ uses $1/f$ and $R_2$ uses 0. We note that if the cylinders were aligned, the beams would always walk off the edge along the flat mirror dimension. Solving for b and γ in Eqn. 10, the formulas for re-entrant theta (single pass) and the stability criteria as discussed earlier become:

$$d = 2f(1-\cos^2\theta_R), \text{ and}$$

$$0 \leq d \leq 2f. \quad (12)$$

Valid solutions can be characterized as N=8M+K for this system where $\theta_R$ is equal to πM/N for an on-axis input hole (linear patterns) and 2πM/N for off-axis entry (elliptical patterns). As with the normal spherical mirror cell, additional restrictions on allowed values of K exist to avoid common factors upon re-entry. The additional restriction for a center (on-axis) hole is that N/2 must be odd.

Figure 5:
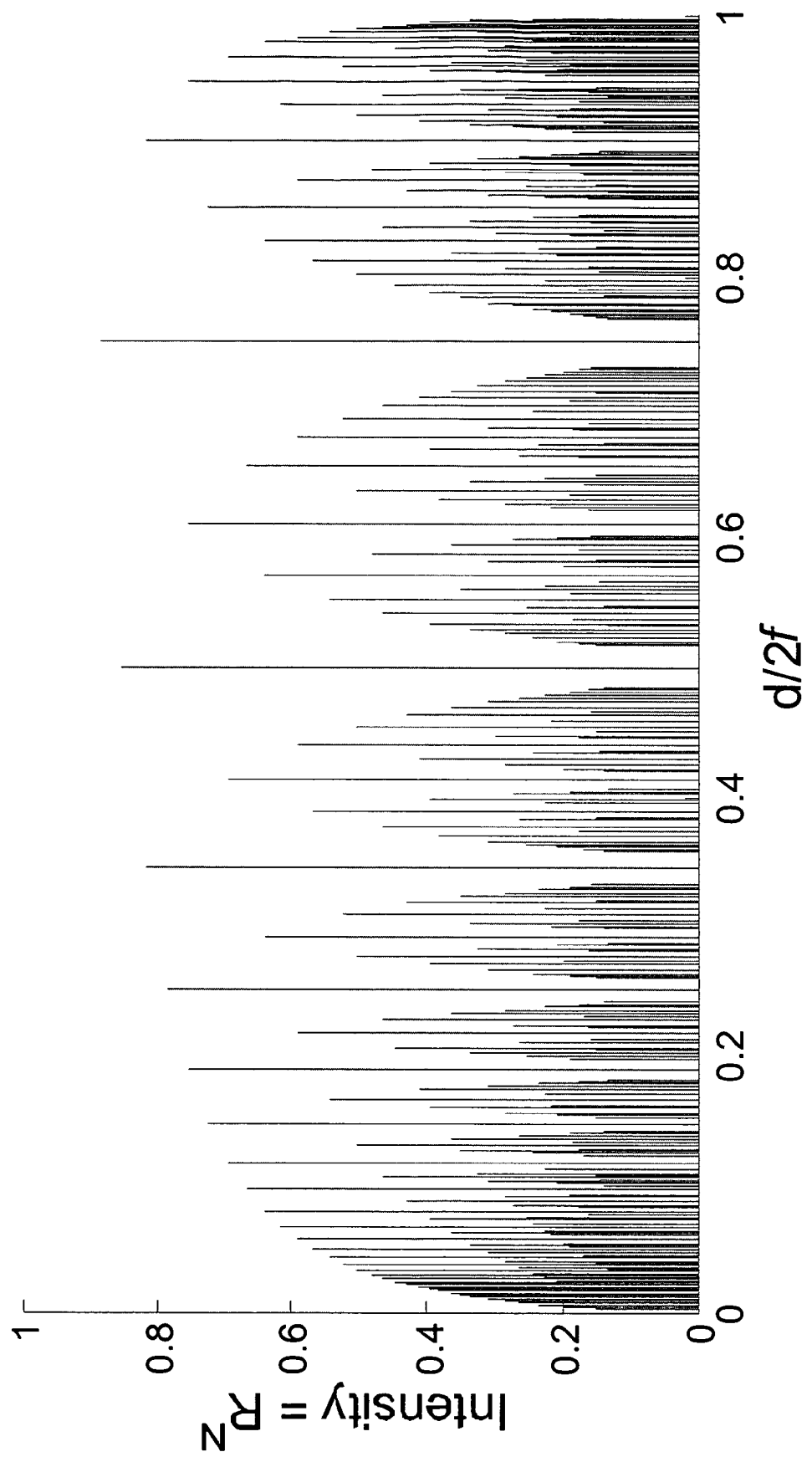
FIG. 5 is a plot of the patterns of allowed re-entrant passes for a cylindrical mirror cell as a function of dimensionless mirror separation d/2f, with the mirror axes at 90 degrees and an off-axis input hole. The transmitted intensity is equal to $R^N$, where R is the reflectivity of the mirrors (0.98 here) and N the total number of passes through the cell.

In all prior uses of spherical and astigmatic Herriott cells, for optimal results the light was injected through the input mirrors with normalized slopes $x_0'=\pm1$, $y_0'=\pm1$ for on-axis systems ($x_0=0$, $y_0=0$) and $x_0'=\pm1$, $y_0'=-1$ for off-axis cells (relative to $x_0=0$, $y_0=1$). However for cylindrical mirror cells, we find more a useful input slope condition to be $x_0'=\pm1$, $y_0'=0$ for both on- and off-axis systems, relative to the input configurations presented. These create the widest dispersion and greatest symmetry of spot patterns. FIG. 5 shows the allowed patterns of spots for a cylindrical mirror cell at 90 degrees with an off-axis hole. Again, the relative intensity of the light exiting the cell is related to N by $R^N$, where R=0.98 is the mirror reflectivity in this calculation. Notice that the allowed patterns of N are similar, but not identical, to those of the spherical cell.

If one of the mirrors is now rotated away from 90 degrees to get dense patterns, the 4×4 matrix or the more detailed analytic solutions are required to predict and compute spot patterns and re-entrant conditions. For two cylindrical mirrors of equal focal lengths, it is useful to describe the re-entrant angles as a function of the input parameters, $$\cos(2\theta_{xR}) = \frac{1}{2}(F - \xi), \text{ and}$$

$$\cos(2\theta_{yR}) = \frac{1}{2}(G - \xi),$$

where $$F = 2\left[\left[\left(\frac{d}{f}\cos^2\tau - 1\right)^2\right] - \left(\frac{d}{f}\right)^2\cos^2\tau\right],$$

$$G = 2\left[\left[\left(\frac{d}{f}\sin^2\tau - 1\right)^2\right] - \left(\frac{d}{f}\right)^2\sin^2\tau\right],$$

$$\zeta\xi = \frac{1}{2}\left\{(G-F)\left[-1 + \sqrt{1 - \frac{4\varepsilon^2}{(G-F)^2}}\right]\right\}, \text{ and}$$

$$\varepsilon = -\left(\frac{d}{2f}\right)^2 \sin(4\tau r) \text{ and } \tau = \delta/2.$$

Given a set of mirrors with focal lengths f and a desired set of advance angles $\theta_x$, $\theta_y$ (i.e. given $M_x$, $M_y$ and N), one can solve these equations to determine the necessary mirror separation d and twist angle δ needed to achieve this pattern. Note that all solutions depend only on the ratio of d/f, not on the absolute value of the focal length as for an astigmatic or unequal cylindrical cell.

Using reduced co-ordinates for mirror separation (z=d/f), one can compute plots of spot patterns on each mirror for any values of d and δ. Examination of these patterns in terms of input conditions, exit slopes, overlapping spot patterns, etc. allow us to characterize this matched cylindrical system as follows. In the discussion that follows, we assume that the input ("front") mirror will be rotated away from the orthogonal axes (having a central input hole), that the curvature on this mirror is in the y-z plane and that the curvature on the rear mirror is in the x-z plane. Exchanging the x and y curvatures for these mirrors, or having the rear mirror rotate does not affect the behavior or solutions, only the particular intermediate spot positions, which can be readily calculated for any configuration using the matrix formulation.

Center Input Hole Solutions

For a central input hole, any input slopes that keep the pattern on the mirrors is useful. However, we find that the optimal input slope for both cases for a cylindrical mirror pair is one where the first pass spot position is $x_1=\pm1$ and $y_1=0$ (given $x_0'=\pm1$, $y_0'=0$). In practice, this means that the first spot (N=1) is pointed to a co-ordinate position of just less than half the mirror radius at a mirror separation of d=f. Under these conditions, the mirror areas are most efficiently filled to allow the highest density of spots and patterns are more square.

There are re-entrant solutions for all integer values of $M_x$ and $M_y$. N is even since we only consider here solutions with one mirror hole. However, not all allowed solutions are equally useful, and there are three categories for $M_x$, $M_y$ pairs.

First, the most useful case is where both $M_x$ and $M_y$ are even integers. In this case the beam always exits as the mirror image of the input beam relative to the input plane. For example, if the input beam position some distance behind the front input mirror hole is at co-ordinates $x_{in}$, $y_{in}$, then the output beam at the same distance from the mirror will be found at $-x_{in}$, $-y_{in}$. Also, the output spot is essentially invariant to minor misadjustments to the mirror tilt alignment for this case, similar to the behavior for spherical Herriott cells with this re-entrant behavior (equal coefficients along the diagonal of the transfer matrix $C_{N/2}$). Within this case, we also find that the N/2 spot always lies at the mirror center ($x_{N/2}=0$, $y_{N/2}=0$). For N/2=even, the (N/2)$^{th}$ spot always lies on the front mirror and would exit early on this pass, rather than on the N$^{th}$ pass; thus these patterns of N are not allowed. However, for N/2=odd, the N/2$^{th}$ spot will always be found at the rear mirror center position. This is very useful for recognizing when a valid re-entrant pattern is achieved.

Second, if $M_x$ and $M_y$ are both odd numbers, then the re-entrant output beam always exits back along the exact input beam path and will travel back to the light source. While not useful for absorption measurements, this may be very useful for applications where a long optical feedback path returning to the laser source is desired.

The final case occurs when $M_x$ is even and $M_y$ is odd, or vice versa, the output beam exits the cell at co-ordinates that vary in the x-y plane, depending on the values of $M_x$, $M_y$ and N. Since there is no simple a priori prediction of where these positions lie, this is considered less useful than the first case for applications that would typically benefit from a Herriott-style cell (using either spherical or astigmatic mirrors).

A further restriction on allowed spot patterns is degeneracy of higher order patterns which are multiples of lower order patterns. Similar to the modulo K restrictions of spherical and astigmatic cells, we find that for N/2=odd patterns, solutions where $M_x$ and $M_y$ are both a multiple of the same prime factor of N (other than 2) are not allowed. For example, if N=42, then 3 and 7 are prime factors of N. Solutions with $M_x=14$, $M_y=14$ or $M_x=6$, $M_y=12$ would not be valid ($M_x$ and $M_y$ are both multiples of the same prime number 7 or 3, respectively), but $M_x=14$, $M_y=12$ is allowed since $M_x$ and $M_y$ relate to different prime factors of N. For M pairs other than even-even, similar restrictions also apply.

Figure 6:
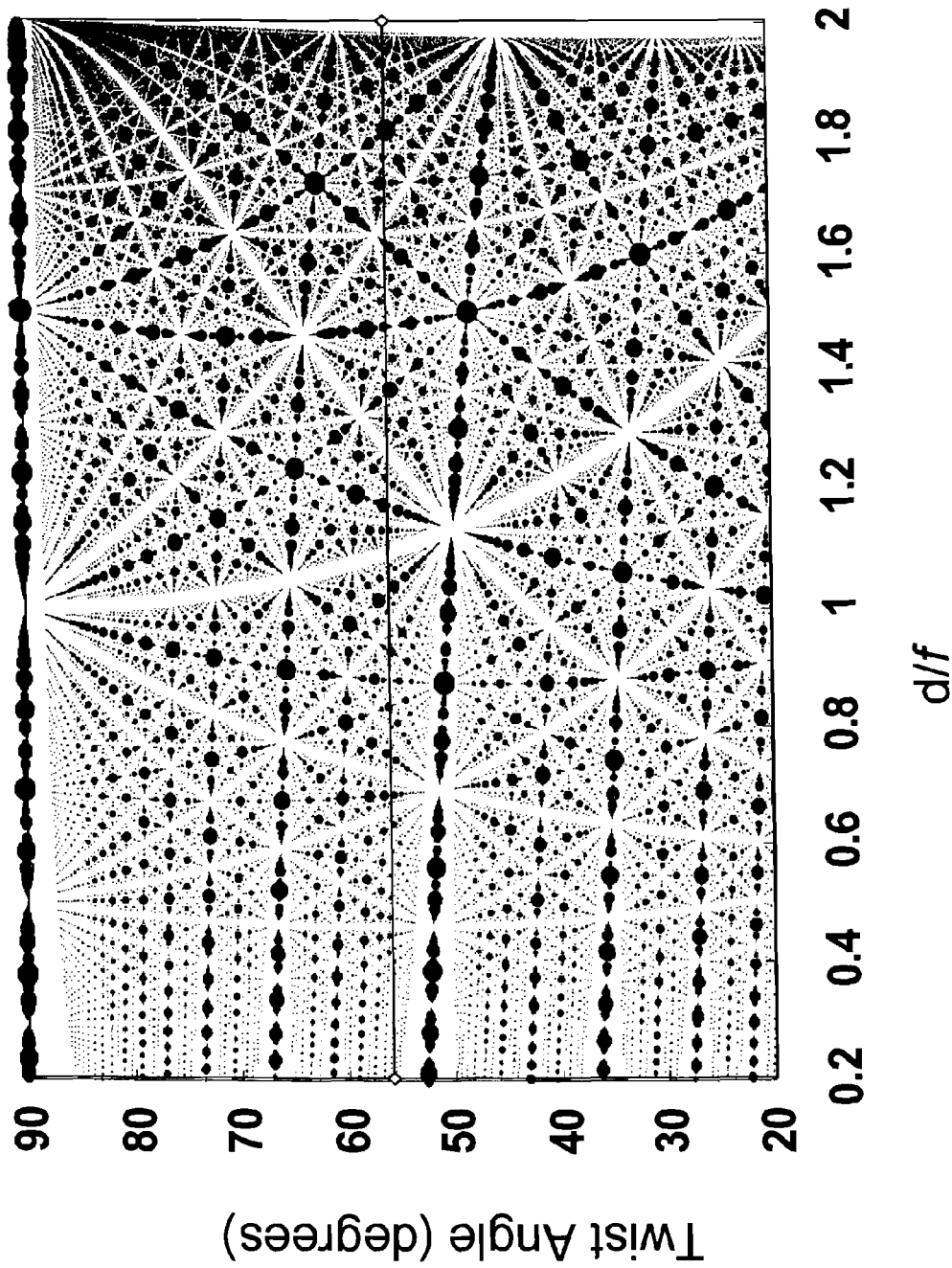
FIG. 6 is a map of the number of allowed re-entrant passes as a function of dimensionless mirror separation d/f and mirror twist angle δ. The magnitude of N is denoted (logarithmically) by the diameter of each spot. The largest spot corresponds to 4 passes and the smallest to 250 passes.

FIG. 6 illustrates the map of allowed re-entrant systems for up to 250 passes for a cylindrical mirror cell having a center input hole for $0.2 \leq d/f \leq 1.0$ and 20 degrees $\leq \delta \leq 90$ degrees. The relative sizes of the symbols (on a logarithmic scale) inversely scale as the number of passes N, where N varies from 4 (largest symbol) to 250 (smallest). Clearly, there are many possible solutions for any desired number of passes, independent of the precise value of the focal length.

Off-Axis (Edge) Input Hole Solutions

For an edge input, reasonable slopes are those that cause the spot pattern to be confined to the mirror surfaces. So if $x_0=0$, $y_0=1$, the beam slopes are generally defined so that the spot positions after the first pass are $-1<x_1<1$ and $0<y_1<r$, where r is the radius of the mirror. However, for an initial beam slope having $x'=\pm 1$ and $y'=0$, the spot pattern is optimally spaced and diamond-like for twist angles other than 90 degrees. At 90 degrees, patterns are optimally circular at d=f and follow elliptical paths at other mirror separations similar to the spherical mirror Herriott patterns.

Only even pairs of $M_x$, $M_y$ with N/2=odd give re-entrant solutions for off-axis systems. For odd-odd, even-odd or odd-even pairs, the $N^{th}$ spot hits the front mirror at some multiple of 90 degrees away from the input hole and is not particularly useful. As with all other Herriott-style cells, additional restrictions on M values occur due to lower order degeneracies. Off-axis entry for dense patterns are in general not as useful as the on-axis cells since here there are often spots very close to the input hole.

Understanding Relationships Between M Indices and Spot Patterns

In order to identify spot patterns from observed systems using the computed patterns, it helps to better understand how the variables ($M_x$, $M_y$, N, d and $\delta$) are interrelated. Focusing on the N/2=odd system for now (although these rules apply to all systems), we find that for a stable cavity ($0<d<2f$), $M_x<N/2$, $M_y<N/2$, and $M_x+M_y<N/2$. Since the mirror rotations are symmetric about 90 degrees, so are spot patterns (see FIG. 6). From a mathematical standpoint as the mirror systems of the invention are defined, $M_x>M_y$ correspond to twist angles <90 degrees, $M_x<M_y$ to angles >90 degrees and $M_x=M_y$ to the degenerate system at $\delta=90$ degrees. In general, for any specified N, lower values of $M_x$ and $M_y$ correspond to smaller values of d. Solutions where d~f have indices whose sum is near N/2. The difference $M_x-M_y$ is a measure of the twist angle—large difference correspond to solutions near 0 degrees or 180 degrees, and smaller differences have solutions lying near 90 degrees. Thus if we decide to configure our system for 174 passes and want the mirror separation to be approximately 1.1×f and the twist angle near 80 degrees, these rules help in estimating the values of $M_x$ and $M_y$ which will give this pattern so that the observed pattern can be confirmed readily by a computed figure.

PRESENTLY PREFERRED EMBODIMENT

Figure 4:
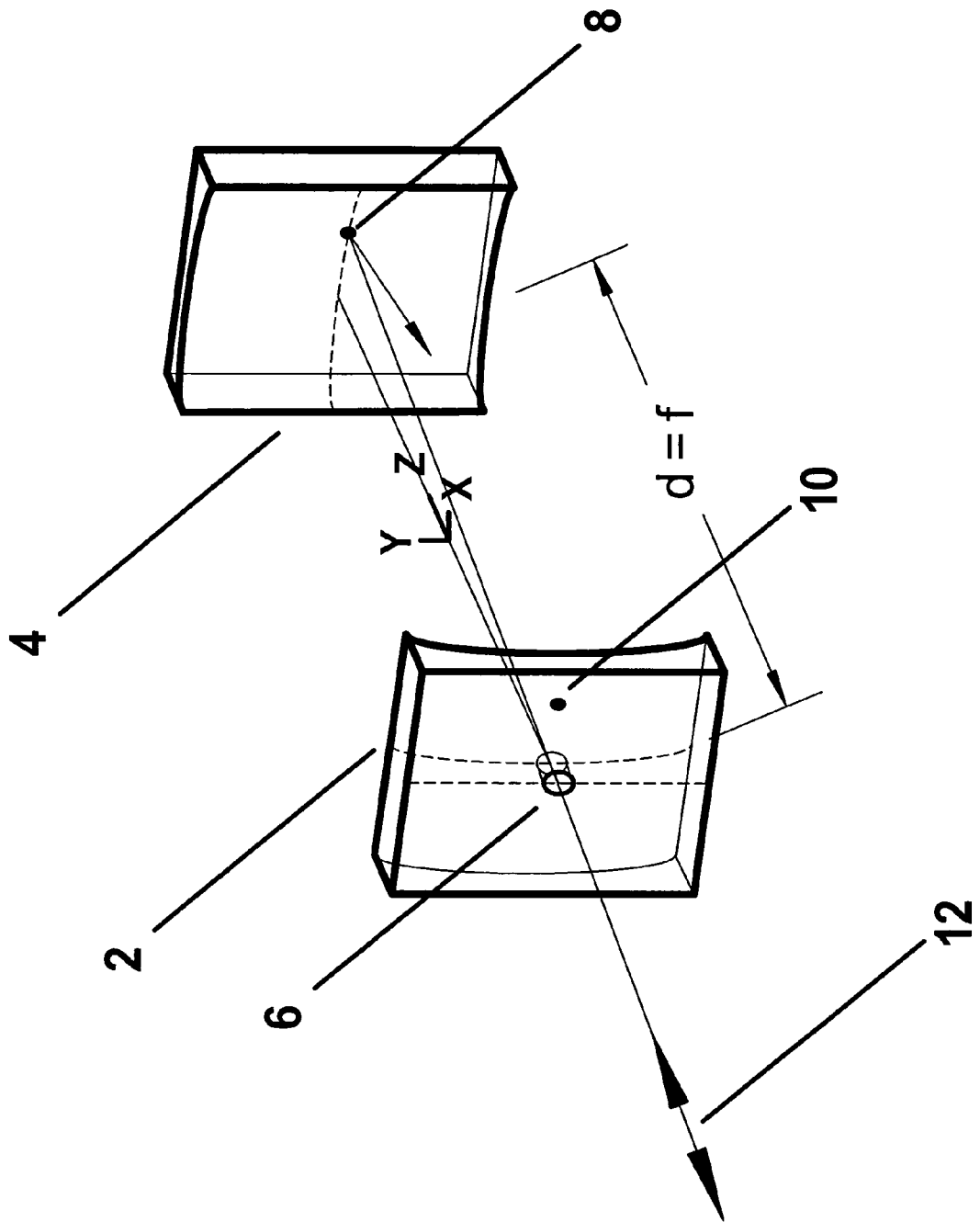
FIG. 4 is a drawing of the cylindrical mirror cell of the invention having a center on-axis input hole.

A pair of commercial 5 cm-square cylindrical mirrors with f=64.8 mm (Newport Corporation, Model 03SI31512) was assembled on mounts on an optical rail so that the separation could be smoothly varied. The front mirror was mounted on a rotation stage to set the twist angle. As illustrated in FIG. 4, the front mirror 2 is aligned so that the radius of curvature is in the y-z plane and the rear mirror 4 initially is set with its radius of curvature in the x-z plane. The output of a JDS Uniphase He—Ne visible laser (632.8 nm) was injected through a 3/16" dia. hole 6 in the center ($x_0=0$, $y_0=0$) of the front mirror such that at d=f, the first spot 8 strikes the rear mirror at $x_1=25$ mm, $y_1=0$ mm (with a slope arbitrarily defined in reduced units as $x_0'=1$, $y_0'=0$). The reflectivity of these mirrors at 632 nm is approximately 0.975. The intensity of the output beam from the cell is monitored by a silicon photodiode (UDT Model Number 2DI).

Using a diode laser or other laser, tuned to a wavelength corresponding to an absorption feature of a selected gas, this cell could be used to measure the concentration of that absorbing gas. For example, a 760 nm laser could be used to monitor the concentration of molecular oxygen in this cell.

Alignment of this mirror pair is simple. Setting the mirrors at approximately d=f (a four pass pattern shown in FIG. 4), the second spot on the front mirror 10 lies directly across from the spot corresponding to the first pass 8 ($x_2=x_1$, $y_2=y_1$), and the third pass reflects directly back onto spot 1 on the rear mirror. The fourth and final pass exits through the input hole along the same path 12 in which the laser beam was injected. This alignment can be verified by observing the exit spot superimposed on the input beam on any of the mirrors that point the incoming beam into the cell. In terms of cell indices, this condition is characterized by $N_{M_y}^{M_x}=4_1^{\ 1}$. As the distance is varied away from d=f, all spot patterns should be observed as horizontal lines. If the pattern appears two dimensional, then a minor twist angle rotation of the front mirror will quickly flatten the pattern to the desired linear shape. This setup defines the 90 degree crossed cylindrical alignment.

If one were using an off-axis entry hole position (such as $x_0=0$, $y_0=1$), then there would be an 8-pass re-entrant condition (N=8, K=0, M=1) with a rectangular pattern on the back mirror and a diamond on the front. Note that this assumes the same beam entry slope as with the center hole scenario. Other input slopes would give different patterns, but all could be calculated and used for initial alignments.

Now using the center-hole input, as the mirror separation is moved away from d=f, a series of linear spot patterns is observed, corresponding to a flattened normal Herriott pattern. As described earlier, the radial input would display elliptical patterns similar to a spherical Herriott cell. Since these spots are easily counted, we can use these as a guide (as well as measure mirror separation) to determine where we are in d-$\delta$ space before rotating the twist angle to achieve dense spot patterns. We also note that the allowed output spot patterns (N/2=odd) have a constant output beam position and we can align the detector now using the output beam for any N/2=odd pattern.

Figure 7:
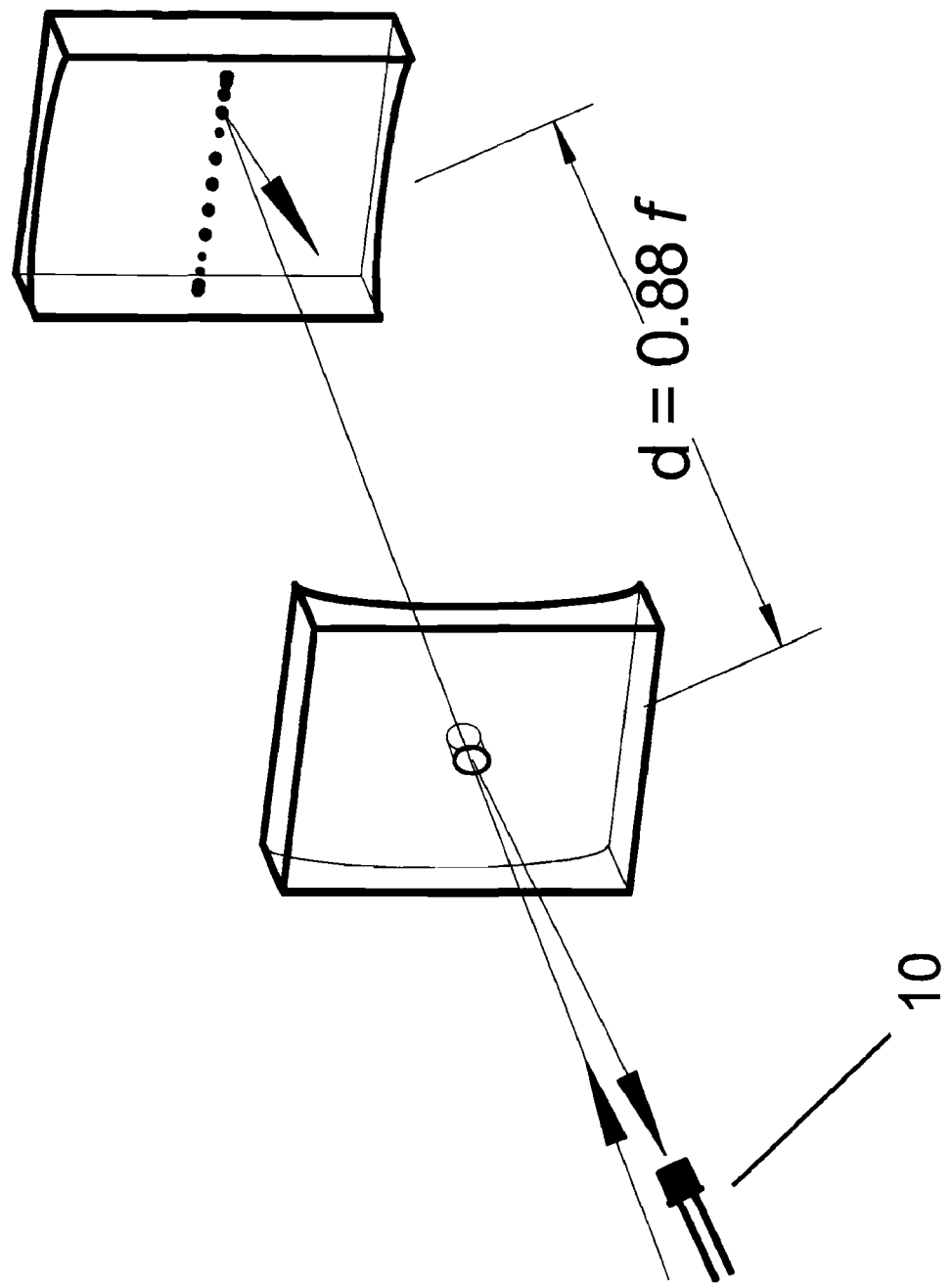
FIG. 7 is a spot pattern computed and observed for 26 passes with a 90 degree crossed cylindrical mirror cell at dimensionless separation 0.88.
Figure 8:
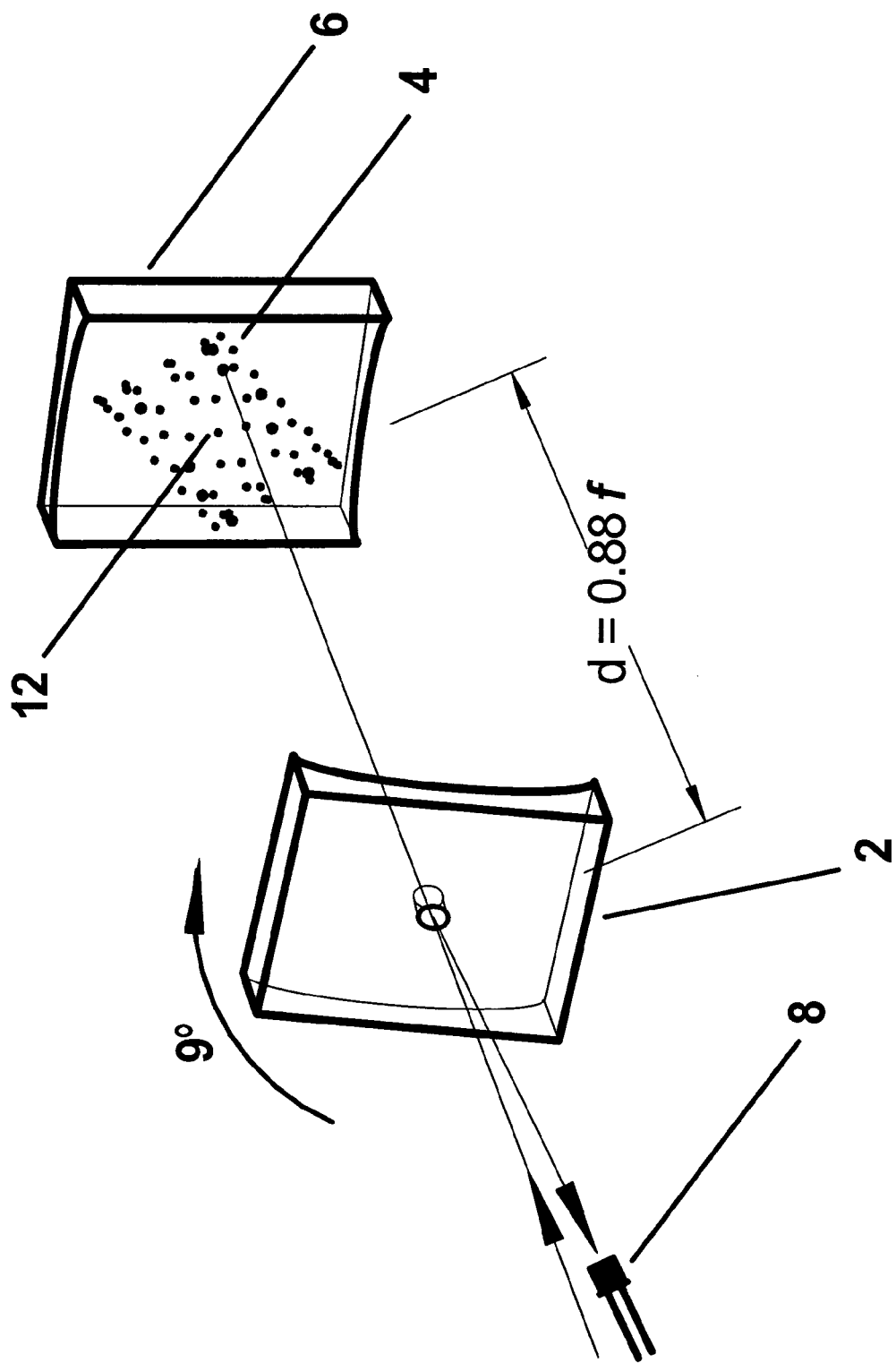
FIG. 8 is a dense spot pattern computed and observed by taking the mirror configuration from FIG. 7 and rotating one mirror by 9 degrees to achieve 122 passes.

FIG. 7 shows an unrotated ($\delta=90$ degrees) spot pattern of N=26 with d/f=0.88, where the beam exits the cell and strikes the photodiode 10. As shown in FIG. 8, by rotating the front mirror 2 by about 9 degrees, a dense 122-pass pattern of spots is formed 4. In this case the final alignment can be made by very minor distance and angle corrections to get the output spot centered on the detector 8.

One aid in identifying allowed patterns is that these all exhibit a centrally located spot 10 ($x_{N/2}=0$, $y_{N/2}=0$) on the rear mirror 12. This spot is always corresponds to the N/2$^{th}$ pass. As with Other Herriott-type cells, this particular configuration is insensitive to mirror tilt. Many similar patterns can be achieved by various combinations of separation and rotation as predicted from the calculations illustrated in FIG. 6.

Figure 9:
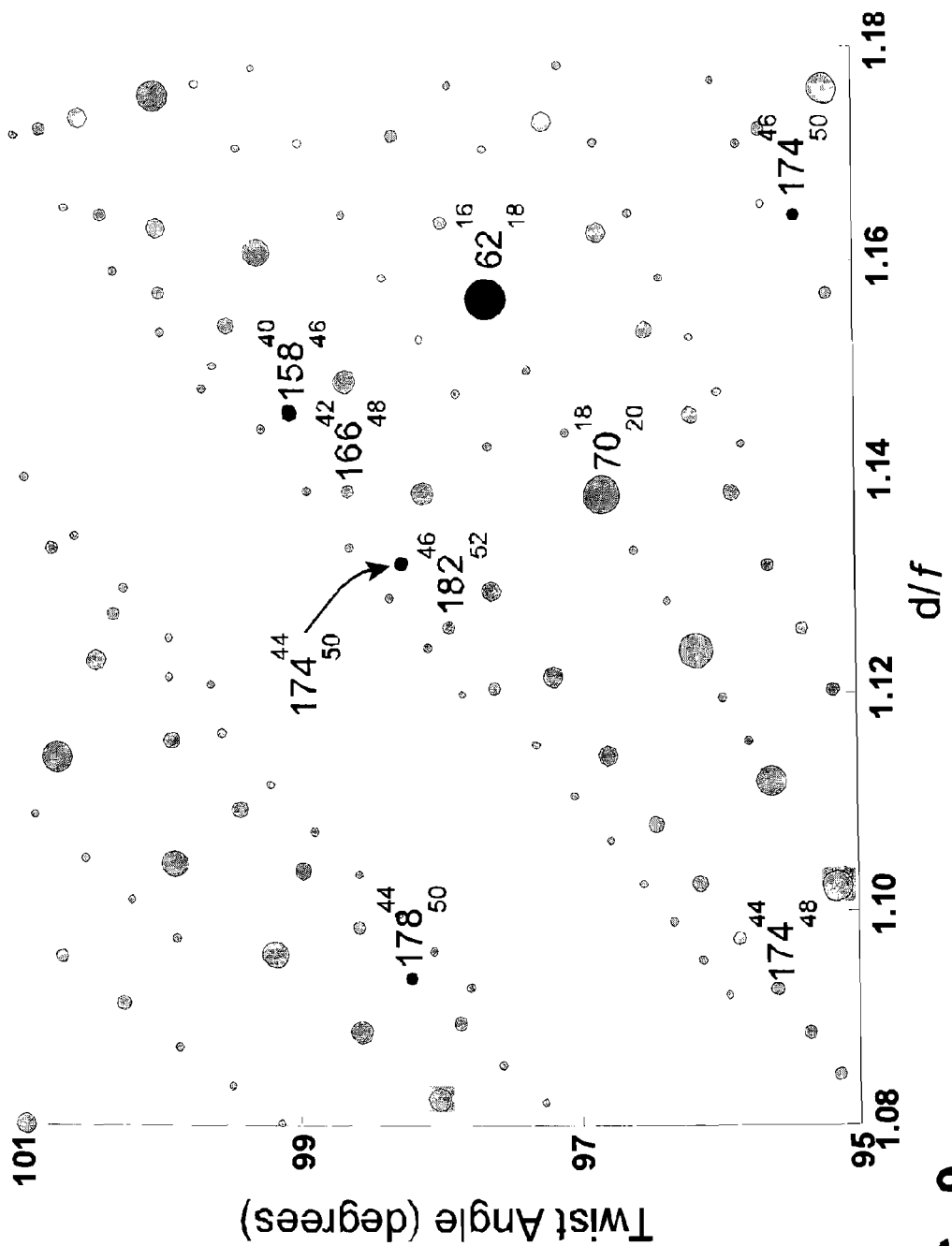
FIG. 9 is a map of the number of allowed re-entrant passes as a function of dimensionless mirror separations d/f near 1.1 and mirror twist angles δ near 98 degrees. Selected spots are darker and denoted by the indices $N_{M_y}^{M_x}$.
Figure 10:
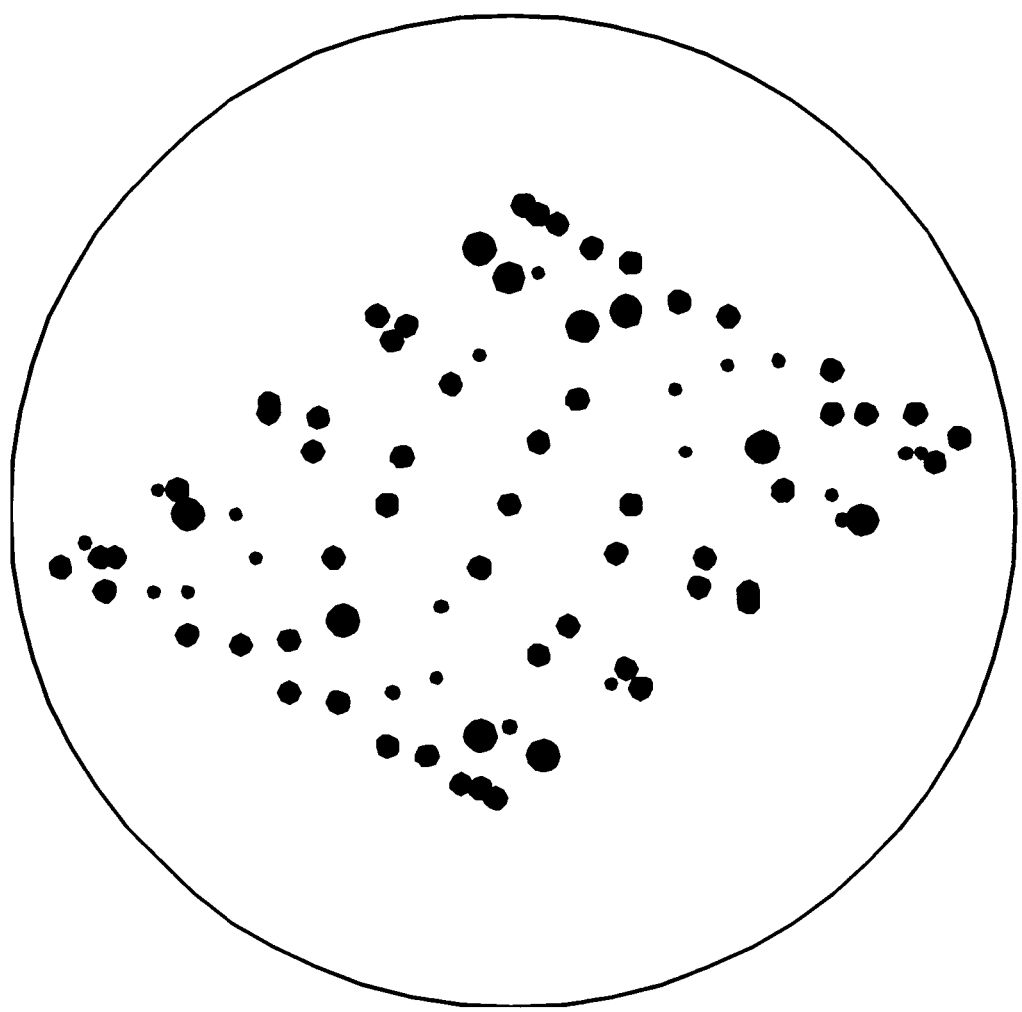
FIG. 10 is a plot of a 174 pass dense spot pattern computed and observed at d/2f=1.13 and mirror twist angles δ=98.3 degrees.

For example, if we look in FIG. 9 at an enlarged portion of FIG. 6 near d=1.1f and $\delta=98$ degrees, one sees that a moderate number of solutions exists, but that the $N_{M_y}^{M_x}=174_{50}^{\ 44}$ system should be positioned at z=1.132 and δ=98.25 degrees. From the formulas (either matrix or analytic) we can compute the expected spot pattern shown in FIG. 10. Then adjust the mirror system to the region of z-δ space until the output spot hits the detector and the pattern matches this computation. Conversely, one can also just set the mirrors to some desired pattern and then computationally identify N, $M_x$ and $M_y$.

The increased symmetry of the cylindrical cell permits the possibility of much easier alignment and assignment of patterns, and certainly more flexibility in choosing patterns for a given system. In the astigmatic cell, there is, in general, only a single allowed exact solution for a given mirror pair, where d is determined from the defined N for the cell given by $f_x$ and $f_y$. The cylindrical cell permits virtually any solution for a given mirror pair, since the solutions depend on the ratio of d to f, not on the absolute value of f.

Unlike the astigmatic or mismatched cylindrical cell, achieving alignment of these spot patterns does not rely on the absolute manufactured focal lengths, but only on ratio d/f, which is easily adjusted by varying the mirror separation. Whenever, $M_x=M_y$, the system is degenerate and all solutions are those of the 90 degree crossed cylindrical mirror system.

Neither the input hole nor slope is restricted, except by physical dimensions to be sure that all spots hit a mirrored surface. However, the better choices for input hole locations are in the center. As discussed earlier, the re-entrant conditions differ slightly by whether multiples of π (center) or 2π(edge) define the mapping of the spot patterns before exiting.

Note that the following variations may be employed:

(1) Different focal lengths on each mirror change patterns, spot sizes, stability criteria, but do not change overall usefulness (i.e., both mirror focal lengths do not have to be critically matched to each other or the design value).

(2) Using other input slopes—just changes spot pattern shapes.

(3) Non-central input holes—similar patterns, different restrictions; discussed above.

(4) Separate input and output holes—output hole can be used to pick off pass number N'<N if properly positioned.

(5) Not restricted to even $M_x$–even $M_y$ patterns. One can use even-odd or odd-even. The special case of odd-odd is particularly useful for long path feedback signal into laser source.

(6) Any stable cavity distance from d>0 to d≦2f is allowed and possible, although solutions in range 0.5≦d/f<1.5 are most useful based on relative pattern diameter and useful total path lengths.

(7) Input beam focus generally collimated or focused to some point into cell. It is often desirable to focus at midpoint of mirror separation so that all spots have approximately same diameter. In any case, output beam focusing properties can be described to appear as though the input beam just reflected off the input hole as if it were a flat mirror.

(8) Cell may be enclosed in sealed container to sample externally introduced gases or be open to the air for ambient sampling.

(9) Either mirror can be rotated relative to the other.

INDUSTRIAL APPLICABILITY

The invention is further illustrated by the following non-limiting examples.

EXAMPLE 1

The same cylindrical mirror cell as above except that the input hole is near the edge of the mirror.

EXAMPLE 2

An intracavity absorption cell could be constructed by using $M_x$=odd, $M_y$=odd spot patterns, where the exiting light automatically feeds back into the laser.

EXAMPLE 3

Set up the cylindrical mirrors at 90 degrees and use the cell in the same manner as one would use a conventional spherical mirror Herriott cell for absorption or other optical experiments or measurements.

EXAMPLE 4

Set up the cylindrical mirrors at 90 degrees and utilize the property that the spot patterns formed are exactly linear to make one-dimensional measurements across a plane. This is useful for concentration measurements in premixed flames that use a flat flame burner, where the concentrations of species vary in the vertical (y) axis, but are uniformly distributed in the x-z plane. The very long path achievable makes possible the measurement of species that are important to flame chemistry but have very low concentrations or weak absorptions.

EXAMPLE 5

A mirror pair consisting of one spherical and one cylindrical mirror can also exhibit dense Lissajous patterns of spots, despite the fact that this system is invariant to rotation angle.

EXAMPLE 6

A mirror pair consisting of one astigmatic and one cylindrical mirror can also exhibit dense Lissajous patterns of spots.

EXAMPLE 7

A cylindrical mirror cell where a second hole is positioned at some spot location <N. This may be useful if the detector is large or needs to be more physically separated from the input optics that point the laser into the cell. For example, one could design a cell with holes in the center of both mirrors and put the detector behind the rear mirror hole, achieving N/2 passes for any given allowed setup conditions.

EXAMPLE 8

A cylindrical mirror cell where re-entrant requirements are not met, or where the beam does not exit through the hole until after very many passes. This may be very useful for cavity ringdown or photoacoustic absorption experiments where very long paths are desired and the laser beam does not need to be directly detected.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A multiple pass optical cell comprising a pair of opposed spherical cylindrical mirrors having curved axes with substantially equal focal lengths, an entrance hole for introducing light into the cell at approximately a center of one of said cylindrical mirrors, and an exit hole for extracting light from the cell, wherein said entrance hole and exit hole are coextensive or non-coextensive, and wherein said curved axes are crossed at angles other than approximately 0, 90, 180, and 270 degrees.

2. The optical cell of claim 1 additionally comprising a rotation mount for one of said mirrors permitting rotation of said curved axes with respect to one another.

3. The optical cell of claim 1 wherein a plurality of number of passes of light between the two mirrors exist for light entering said entrance hole and exiting said exit hole for any given combination of mirror separation distance and angle of crossing of said curved axes.

4. The optical cell of claim 1 wherein manufacturing tolerances as to said focal lengths are adjusted for by varying mirror separation distance.

5. A multiple pass optical cell comprising a pair of opposed cylindrical mirrors having curved axes crossed at angles other than approximately 0, 90, 180, and 270 degrees, an entrance hole for introducing light into the cell, and an exit hole for extracting light from the cell, wherein said entrance hole and exit hole are coextensive or non-coextensive and wherein light is introduced through the center of one of said cylindrical mirrors.

6. The optical cell of claim 5 wherein said curved axes have substantially equal focal lengths.

7. The optical cell of claim 6 wherein manufacturing tolerances as to said focal lengths are adjusted for by varying mirror separation distance.

8. The optical cell of claim 5 additionally comprising a rotation mount for one of said mirrors permitting rotation of said curved axes with respect to one another.

9. The optical cell of claim 5 wherein a plurality of number of passes of light between the two mirrors exist for light entering said entrance hole and exiting said exit hole for any given combination of mirror separation distance and angle of crossing of said curved axes.

10. A multiple pass optical cell method comprising the steps of:
providing a pair of opposed spherical cylindrical mirrors having curved axes with substantially equal focal lengths;
positioning an entrance hole for introducing light into the cell at approximately a center of one of the cylindrical mirrors and an exit hole for extracting light from the cell, wherein the entrance hole and exit hole are coextensive or non-coextensive;
introducing light into the cell through the entrance hole; and
extracting light from the cell through the exit hole; and
wherein the curved axes are crossed at angles other than approximately 0, 90, 180, and 270 degrees.

11. The method of claim 10 additionally comprising the step of providing a rotation mount for one of the mirrors permitting rotation of the curved axes with respect to one another.

12. The method of claim 10 wherein a plurality of number of passes of light between the two mirrors exist for light entering the entrance hose and exiting the exit hole for any given combination of mirror separation distance and angle of crossing of the curved axes.

13. The method of claim 10 wherein manufacturing tolerances as to the focal lengths are adjusted for by varying mirror separation distance.

14. A multiple pass optical cell method comprising the steps of:
providing a pair of opposed cylindrical mirrors having curved axes crossed at angles other than approximately 0, 90, 180, and 270 degrees;
positioning an entrance hole for introducing light into the cell and an exit hole for extracting light from the cell, wherein the entrance hole and exit hole are coextensive or non-coextensive;
introducing light into the center of one of the cylindrical mirrors;
introducing light into the cell through the entrance hole; and
extracting light from the cell through the exit hole.

15. The method of claim 14 wherein the curved axes have substantially equal focal lengths.

16. The method of claim 15 wherein manufacturing tolerances as to the focal lengths are adjusted for by varying mirror separation distance.

17. The method of claim 14 additionally comprising the step of providing a rotation mount for one of the mirrors permitting rotation of the curved axes with respect to one another.

18. The method of claim 14 wherein a plurality of number of passes of light between the two mirrors exist for light entering the entrance hole and exiting the exit hole for any given combination of mirror separation distance and angle of crossing of the curved axes.

* * * * *

UNITED STATES PATENT AND TRADEMARK OFFICE
CERTIFICATE OF CORRECTION

PATENT NO. : 7,477,377 B2
APPLICATION NO. : 10/896608
DATED : January 13, 2009
INVENTOR(S) : Joel A. Silver It is certified that error appears in the above-identified patent and that said Letters Patent is hereby corrected as shown below:

Column 7, line 4, delete "a window 18" and substitute --a window 26--

Column 10, line 40, delete "
$$T(\theta_{fw})(\delta) = \begin{bmatrix} \cos\delta & 0 & \sin\delta & 0 \\ 0 & \cos\delta & 0 & \sin\delta \\ -\sin\delta & 0 & \cos\delta & 0 \\ 0 & -\sin\delta & 0 & \cos\delta \end{bmatrix}.$$
"

and substitute --
$$T(\delta) = \begin{bmatrix} \cos\delta & 0 & \sin\delta & 0 \\ 0 & \cos\delta & 0 & \sin\delta \\ -\sin\delta & 0 & \cos\delta & 0 \\ 0 & -\sin\delta & 0 & \cos\delta \end{bmatrix}.$$
--

Column 11, line 55, delete "$\xi = \frac{1}{2}\left\{(G-F)\left[-1+\sqrt{1-\frac{4\varepsilon^2}{(G-F)^2}}\right]\right\}$, and"

and substitute -- $\xi = \frac{1}{2}\left\{(G-F)\left[-1+\sqrt{1-\frac{4\varepsilon^2}{(G-F)^2}}\right]\right\}$, and--

Column 11, line 57, delete "$\varepsilon = -\left(\frac{d}{2f}\right)^2 \sin(4\tau)$ and $\tau = \delta/2.$"

and substitute -- $\varepsilon = -\left(\frac{d}{2f}\right)^2 \sin(4\tau)$ and $\tau = \delta/2.$ --

UNITED STATES PATENT AND TRADEMARK OFFICE
CERTIFICATE OF CORRECTION

PATENT NO. : 7,477,377 B2
APPLICATION NO. : 10/896608
DATED : January 13, 2009
INVENTOR(S) : Joel A. Silver It is certified that error appears in the above-identified patent and that said Letters Patent is hereby corrected as shown below:

Column 13, line 8, delete " $0.2 \leq d/2f \leq 1.0$ " and substitute --$0.2 \leq d/f \leq 2.0$--

Column 14, line 61, delete "Other" and substitute --other--

Signed and Sealed this

Seventh Day of July, 2009

JOHN DOLL
*Acting Director of the United States Patent and Trademark Office*